United States Patent [19]

Rosander

[11] Patent Number: 4,663,035

[45] Date of Patent: May 5, 1987

[54] APPARATUS FOR SEPARATING AIR AND SOLID PARTICLES FROM A LIQUID

[75] Inventor: Jan Rosander, Gothenburg, Sweden

[73] Assignee: Durr Dental GmbH & Co. KG, Bietigheim, Fed. Rep. of Germany

[21] Appl. No.: 740,973

[22] Filed: Jun. 4, 1985

[30] Foreign Application Priority Data

Jun. 20, 1984 [SE] Sweden ................................. 8403299

[51] Int. Cl.$^4$ ............................................ B01D 45/14
[52] U.S. Cl. .................................. 210/167; 210/512.3
[58] Field of Search .................. 210/512.1, 512.3, 513, 210/521, 523, 524, 532.1, 535, 537, 539, 540, 167, 194, 195.1

[56] References Cited

U.S. PATENT DOCUMENTS 1,751,689  3/1930  Enz et al. ......................... 210/512.3
2,777,581  1/1957  Unthank .............................. 210/539

Primary Examiner—Ivars Cintins
Attorney, Agent, or Firm—Collard, Roe & Galgano

[57] ABSTRACT

Apparatus for extracting air and solids from liquid suspensions thereof comprises a vessel assembly having three cylindrical superposed mutually co-axial chambers. Means are provided for introducing suspension into the uppermost chamber and guiding the same into a centrifuge located in the juncture between the intermediate and bottom chambers. Located beneath the centrifuge is a solids collecting vessel. Means are provided for discharging air and cleansed liquid from the vessel through outlet means therefor. The air outlet means is connected to a source of subpressure and the cylindrical chambers are detachably connected together with the aid of suitable fastener means. The uppermost chamber incorporates a dry section through which air is removed from the vessel, and the guide means is constructed to prevent suspension from entering this section.

12 Claims, 4 Drawing Figures

APPARATUS FOR SEPARATING AIR AND SOLID PARTICLES FROM A LIQUID

The present invention relates to a plant or an apparatus adapted to treat a mixture of air, water and various kinds of solid contaminants to remove the air and the contaminants from the mixture and to produce highly pure water which can be passed safely to a conventional sewage network.

Examples of such contaminated aqueous mixtures are those emanating from dental clinics in dental treatment processes. These contaminants include amalgam containing mercury and free metallic mercury, i.e. contaminants which must not or should not be released into a sewage network.

There are known to the art so-called separation tanks adapted for installation in dental surgeries for example and having the dual purpose of evacuating air from an incoming liquid flow of air and contaminants and removing the contaminants from the liquid, whereafter the cleansed liquid, normally water, is passed out of the apparatus or the separation tank and discharged to a connected sewage network. There is normally arranged upstream of the separation apparatus at some suitable location a fine mesh filter which filters-off and collects the majority of the contaminants present in the liquid flow, or at least contaminants of larger size. Such separation tanks are encumbered with a number of disadvantages however. Firstly they are structurally complicated, comprising a plurality of float means, valves and diaphragms in that part of the apparatus where separation of the solid contaminants takes place. These movable components become, with time, laden with different kinds of contaminant or impurity, such as coagulated blood, tissue residues, etc., which ultimately cause operational disturbances and breakdowns in the function of the apparatus. Although these known separation tanks are provided with means which enable them to be flushed to cleanse the interior thereof, the maximum volume of cleansing liquid which can be received is only about 0.5-0.7 l/min, which does not afford a satisfactory rinsing effect. In addition such tanks are only intended to receive the mixture leaving the suction hose placed in the mouth of a patient. The contaminated water leaving the sputum cup or cuspidor of the surgery cannot be passed to these known treatment apparatus, because of the limited capacity of these separation tanks.

Obviously, these drawbacks could be overcome by enlarging the separation tank so that, inter alia, larger quantities of flushing or rinsing liquid could be used. This solution is not viable in practice, however, since it presents serious installation problems and incurs excessively high costs.

An apparatus for separating solely solid particles from contaminated water is known from U.S. Pat. No. 4,356,959. This known separation apparatus has a satisfactory water cleansing efficiency and its separating function is based on the centrifugation of the liquid-carried solid particles in a funnel shaped rotatable container adapted herefor. When the container ceases to rotate, the particulate contaminants settle to the bottom of a collecting vessel. The apparatus has means which enables it to be flushed with a cleansing liquid, although only to a limited extent.

A further apparatus intended for separating heavy metals from sewaqe water is known from SE Pat. No. 7902109-3. This apparatus also utilizes the aforesaid centrifugation/settling principle. Apparently this apparatus cannot be flushed through with rinsing fluid for cleansing purposes.

The prime object of the invention is to provide an apparatus or plant which is adapted to receive and to process a mixture of air, water and different kinds of contaminant, this processing of the mixture involving evacuating the air which accompanies the water, effectively separating the contaminants therefrom, preferably to an extent not less than 98%, and permitting the cleansed water to pass out through an outlet opening.

A further object of the invention is to provide an apparatus which is reliable in operation and the component members of which are of such nature as to render blockages due to the contaminants practically impossible.

Another object of the invention is to provide an apparatus which is able to accommodate a relatively large flow of water despite having small dimensions, preferably a flow of not less than 5-6 l/min. By accommodate is meant the accommodation of both contaminated water to be processed and the inflow of large quantities of cleansing/disinfecting liquid passed through the apparatus to optimally clean the same.

These objects are realized in accordance with the invention by means of an apparatus which is characterized in that the container comprises at least two, preferably three mutually detachably connected cylindrical parts, of which the uppermost part presents the tangentially arranged inlet opening and the evacuation opening co-acting with the source of sub-pressure, this opening being located within an annular space defined radially by a sleeve and an annular shield connected thereto, said shield forming guide means for directing a liquid-/air mixture exiting from the inlet opening; and in that the second cylindrical part presents means for guiding said mixture in towards the centre of the container; and in that the third cylindrical part is arranged to accommodate the outlet opening, the rotatable vessel of known kind, and the similarly known collecting vessel.

The apparatus according to the invention will now be described in more detail with reference to the accompanying drawings, in which FIG. 1 is an axial sectional view of the apparatus;

Figure 1:
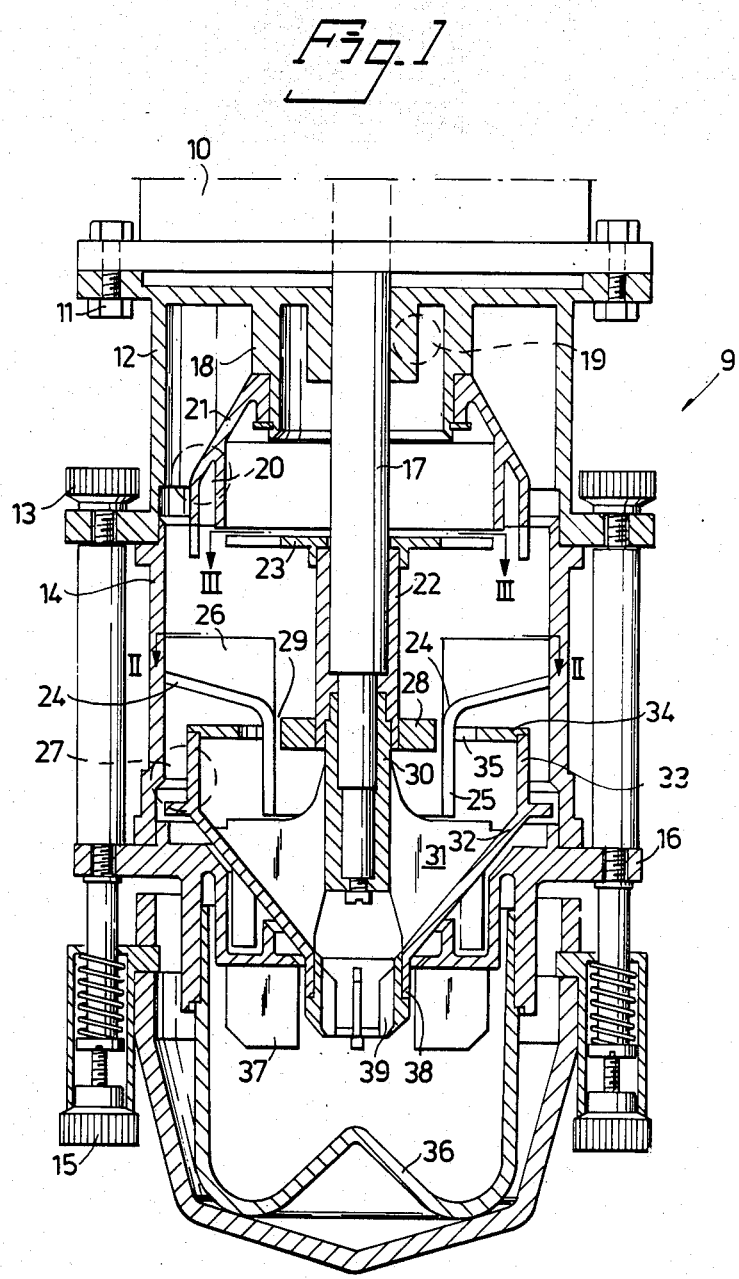
Figure 2:
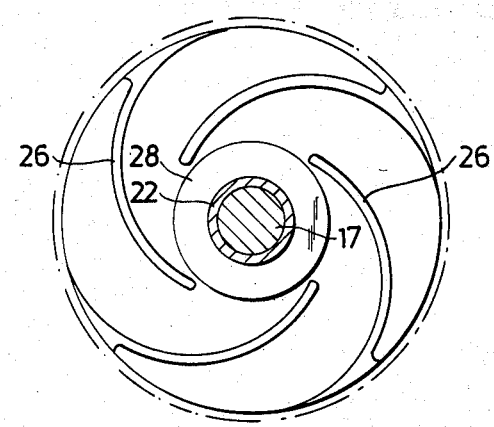
FIG. 2 is a sectional view taken on the line II—II in FIG. 1.
Figure 3:
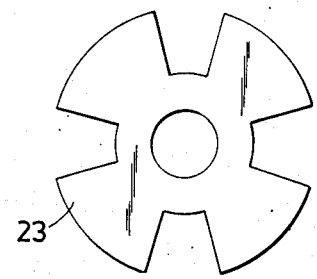
FIG. 3 is a sectional view taken on the line III—III in FIG. 1.

The illustrated apparatus is intended for separating both air and solid particles from a liquid and is installed, for example, in a dental surgery. The apparatus comprises an electric A.C. motor 10 which is connected to an existing electrical network and is detachably bolted through a first set of bolts 11 to a cylindrical container generally referenced 9. The container assembly includes a first cylindrical part 12 which is detachably bolted to a second cylindrical part 14 through a second set of bolts 13, while this second container part is detachably bolted to a third cylindrical part 16 through a third set of bolts 15. The driveshaft 17 of the motor 10 extends centrally through the two first cylindrical parts 12, 14.

The first cylindrical part 12 has a sleeve-like part 18 which surrounds the shaft 17 in this region and which extends downwardly through a given distance. Arranged in the vicinity of the upper part of the cylindrical part 12 on one side of the shaft 17 is an opening 19 which is connected by a conduit incorporating valve means to a suction motor of known design or some other sub-pressure source, the purpose of which is to create a region of sub-pressure in the container 9, as described hereinafter. Located on the opposite side of the shaft 17 at a level lower than the level of the opening 19 is a tangentially directed inlet opening 20 for contaminated water, i.e. water contaminated with saliva, blood, amalgam residues and the like, which are drawn by suction into a conduit connected to the tangential opening 20 through a suction hose placed in the mouth of the patient. This water thus also contains relatively large quantities of air.

The inlet opening 20 is arranged between the inner wall of the cylindrical part 12 and a substantially bifurcate annular part 21 connected to the sleeve-like part 18 and serving as a splash guard, said part 21 extending downwardly and outwardly towards the aforesaid inner wall and terminating beneath the opening 20. The sub-pressure opening 19 is located in the region between the shaft 17 and the sleevelike part 18.

Thus, the bifurcate part 21 confines the incoming contaminated water/air mixture and guides the mixture down through the narrow, or relatively narrow gap formed between the outermost leg of the bifurcate part 21 and the inner wall of the part 12. The underedge of the bifurcate part 21 may have a sawtooth configuration. Driveably connected to the motor shaft 17 is a sleeve 22 on which a perforated disc 23 is arranged for rotation in the border region between the two cylindrical parts 12,14. The disc 23 is also arranged to rotate within the region of the splash guard 21, and located between the outer edge of the splash guard and the inner leg of the bifurcate part is a gap which together with the perforations or openings in the disc 23 serve to guide the air to be evacuated through the opening 19. Consequently, the region between the upper side of the disc 23 and the opening 19 is shielded against liquid in all essential respects. As will be understood, the splash guard 21 and the sleeve-like part 18 may be produced as a one-piece homogenous unit.

Arranged on the inner wall of the second cylindrical part 14 is an annular bifurcate part 24,25 of substantially angular cross-section. This bifurcate part extends radially inwards and downwards, and the leg 24 thereof forms a seat for a plurality of mutually spaced arcuate guide bars 26 which extend from the inner wall and which all open into the space located between the vertical sleeve-like leg 25 of said part and the sleeve 22 surrounding the shaft 17. The lower part of the cylindrical part 14 is also provided with an outlet opening 27 preferably equipped with a non-return valve and arranged between the inner wall of the cylindrical part 14 and the space formed between said inner wall and the vertical leg 25 of said annular part 24, 25. The outlet opening 27 is connected to the sewage network by means of a conduit not shown. The sleeve 22, which rotates with the shaft 17, is provided with a propeller-like means 28 in the juncture between the leg parts 24,25. A relatively narrow gap 29 is formed between the outer edges of the propellerlike means 28 and the sleeve-like leg 25.

The third cylindrical part 16 includes a sleeve 30 which is driven by the motor shaft 17 and which forms an attachment for one side of a plurality of radially extending wings 31, the outer sides of which connect with a funnel-like container 32, the upper widened part of which merges with a circular, upstanding part 33 located substantially between the outlet opening 27 of the second cylindrical part 14 and the sleeve-like leg 25. The upper part of the funnel-like container 32 is terminated in a radially inwardly extending part 34, thereby to form a narrow, circular gap 35 between the end of said part 34 and the downwardly extending sleevelike leg 25. The spaces presented between the radial wings 31 communicate with a detachable collecting vessel 36 which rests on the bottom of the third cylindrical part 16. In the illustrated embodiment there is provided in the region of the collecting vessel 36 a plurality of downwardly extending wings 37. The lower part of the rotatable funnel-shaped container 32 comprises a sleeve-like part 38 which opens into the collecting vessel 36 and which encloses a hollow body 39 having wings provided on its internal surfaces and functioning as pump means for liquid located in the collecting vessel 36. The effect produced herewith is explained hereinafter. The optimal volumetric capacity of the rotatable container 32 is smaller than the volumetric capacity of the collecting vessel 36.

Operational Mode

The aforedescribed plant or apparatus has the following method of operation.

Subsequent to starting-up the apparatus according to the invention, preferably automatically, for example when removing the suction hose from its attachment, the motor 10 causes the shaft 17 and the components connected thereto to rotate in a clockwise direction, i.e. the perforated disc 23, the propeller-like means 28, and the funnel-shaped container 32 provided with the aforesaid radially extending wings. At the same time as the motor 10 is started-up there is opened a valve (FIG. 4) co-acting with the opening 19 in the first cylindrical part 12, and the suction motor or sub-pressure source (not shown) is activated to place the interiors of the cylindrical parts of the apparatus under a suitable sub-pressure, preferably a pressure of about 2 m water column. The non-return valve located in the outlet opening 27 prevents air from being drawn into the system.

As a result of the sub-pressure created in the container, water mixed with air, saliva, tissue residues, amalgam, and the like will flow through the tangential inlet 20 into the cylindrical upper part 12 of the apparatus. This mixture now rotates cyclonically and is forced by the sleeve-part 18 and the splash guard 21 into contact with the inner wall of the second cylindrical part 14, under continued rotation and under the influence of centrifugal force. The narrow gap formed between the rotating perforated disc 23 and the inner wall of the sleeve part 18 forms inlet means for the air contained in the mixture supplied through the opening 20, this air being separated through said components (the disc 23, the splash guard means 18, 21) from remaining constituents of the mixture and is evacuated in a dry state through the opening 19. The sawtooth configuration of the lower edge of the splash guard 21 effectively prevents water droplets from being entrained with the air flow upwardly towards the opening 19, while the configuration of the disc 23 assists in enabling the air to be evacuated without hinder. The disc 23, which rotates with the shaft 17, has an amplifying function and also prevents foam or slime and water splashes from moving upwardly. Consequently, from a functional aspect, the vertical annular space between the opening 19 and the rotary disc 23 can be said to form a dry part of the apparatus.

At the same time as the dry air is evacuated through the opening 19 in the aforedescribed manner, the water and contaminants contained therein sink gravitationally into contact with the guide bars or vanes 26, which are curved in a direction opposite to the rotational direction of the shaft 17, wherewith the water/contaminant mixture is guided rapidly through the spaces located between the guide vanes 26 inwardly towards the centre of the apparatus, and passes the propeller-like means 28 which ensures rapid transportation of the liquid down through the narrow gap 29, from whence it is brought by the rotating container 32 and forced by rotation outwardly into contact with the inner wall of the container 32. This process is made more effective by the rotor-like means 31. The water and particles of low density are able to pass over the edge part 34 of the container 32 and, subsequent to the check valve in the opening 27 being opened by the pressure exerted by the water, the water and low-density contaminants are discharged via the gap 35 out through the opening 27. In this regard, the wings 31 together with remaining parts of the container 32 generate a requisite increase in pressure, to produce a pumping effect which enables the water to pass the check valve and out through the opening 27 and into the sewage network, despite the low pressure prevailing.

Particles of high density, for example metal particles, remain within the container 32 and are pressed under rotation against the wall 33.

When the current to the motor is switched off, for example by disconnecting the function of the suction hose, the valve to the vacuum opening 19 is closed and the power to the sub-pressure source interrupted at the same time as known means co-acting with the motor shaft slow the rotational speed of the shaft from a suitable speed of about 2,700 rpm to 0 rpm in a fraction of a second. This extremely abrupt braking of the shaft speed can be effected by supplying the motor 10 with a direct current pulse, and affords the advantage that the solid particles held pressed by rotation against the inner wall of the container 32, together with any liquid remaining in said container, continue to rotate despite cessation of the rotation of the container 32 itself. This prevents the solid particles from biting into the wall of the container 32 and hence the container is, to a very large extent, self-cleansing, although this cleansing effect can be further enhanced by loosely attaching slip rings to the inner wall of the container 32. The mixture of water and contaminants then passes gravitationally into the collecting vessel 36, with the contaminants settling on the bottom of the vessel. Because the volume of liquid enclosed in the funnel-shaped container 32 is smaller or substantially smaller than the amount of liquid which can optimally be accommodated by the collecting vessel 36, there is no risk of overfilling the last-mentioned vessel.

When the aforedescribed sequence of events is repeated, by re-starting the motor 10, the wing-provided body 39 will function as a pump, by drawing a given amount of liquid into the rotating container 32 by suction. In this regard, the downwardly directed wings 37 serve to prevent the mixture in the collecting vessel 36 from being rotated, and the particles collected on the bottom of the vessel will remain undisturbed. The liquid drawn into the apparatus by suction in the aforedescribed manner comprises mainly solely water mixed by with newly supplied liquid, while the heavy particles remain on the bottom of the vessel 36. Consequently it is not necessary to empty the vessel 36 daily. The particles collected in the vessel 36 can be removed therefrom and any mercury or precious metals present recovered.

The illustrated and described apparatus or plant is adapted to receive solid particles having a particle size of up to 4–5 mm. It is assumed that particles larger than 4–5 mm are filtered-off in a coarse-mesh filter at some suitable location in the plant according to the invention.

The apparatus according to the invention can be readily serviced. The bolt connections between the various cylindrical parts of the apparatus enable ready dismantling for service purposes, for example should larger particles than the aforementioned maximum size enter the apparatus and become fastened in any of the gaps not dimensioned for particles of that size.

Other important functions of the apparatus according to the invention, namely the ability of the apparatus to accommodate liquid volumes not below 5–6 l/min for cleansing and disinfecting purposes are illustrated schematically in FIG. 4, to which reference is now made.

Figure 4:
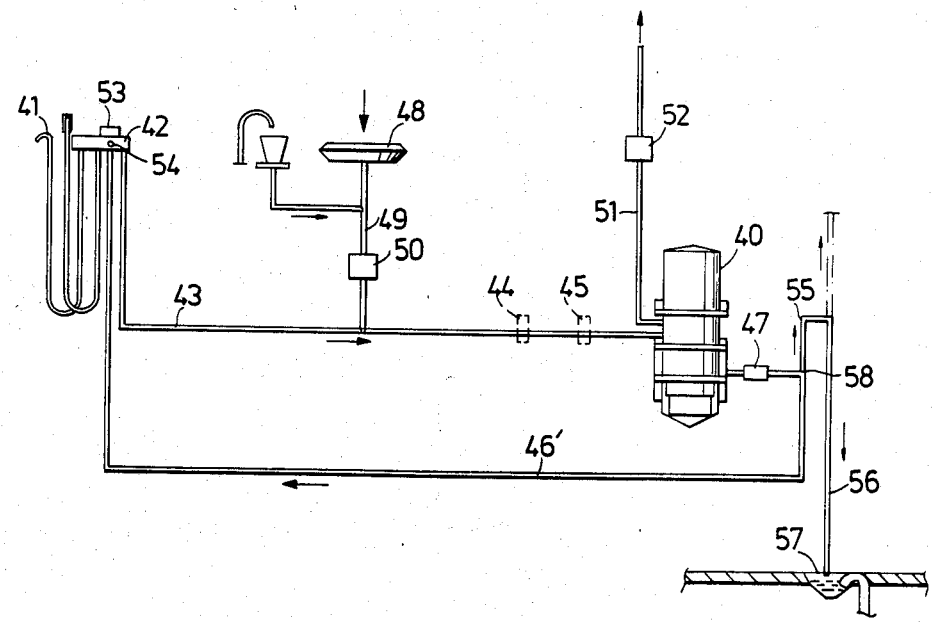
FIG. 4 illustrates schematically the installation of an apparatus according to the invention installed in a dental surgery and connected to treatment units or assemblies having means for effectively cleansing the apparatus and associated conduits.

In FIG. 4 the apparatus illustrated in FIG. 1 is referenced 40. In order to achieve the aforesaid purpose the suction hoses 41 located in a dental surgery are connected to a cycling connection 42. A vacuum pipe 43 connects the apparatus 40 with the suction unit 41. The arrows shown on the pipe 43 indicate the direction of flow, and the system may incorporate a disposable filter 44 or a protective filter 45. Extending from the apparatus 40 is an outlet pipe 46, while the reference 47 identifies a non-return valve connected downstream of the apparatus 40. The system incorporates a water-flushed cuspidor 48 which is connected by a pipe 49 to the vacuum pipe 43. The pipe 49 incorporates a vacuum valve 50. The reference 51 identifies the pipe or conduit through which air is evacuated from the contaminated liquid in accordance with the aforegoing, said pipe incorporating a vacuum valve 52.

A cleansing and disinfecting fluid is supplied, for example, to the cuspidor 48. The volume of liquid supplied is determined by the length and diameter of the pipes or conduits, and it is possible to check visually through an inspection window 53 that the liquid circulates in the manner intended, i.e. that the liquid is drawn into the apparatus 40 by the vacuum valve 50 and the vacuum pipe 43. This liquid is introduced to the interior of the apparatus 40 in the aforedescribed manner, whereafter the liquid is pumped from the apparatus to a return pipe 46', which forcibly recycles the liquid under the action of the suction unit 41.

In order to provide the best possible result, the cleansing liquid in circulation should be mixed with air, this being effected, for example, by providing the cycling connection 42 with an air intake, indicated at 54. It is important with respect to cleansing and disinfecting the apparatus that the liquid is caused to circulate and therewith wear against the inner surfaces of the pipes or conduits over a given length of time. A "liquid flow" of about 5–6 l/min. can be obtained by supplying one liter of liquid and causing the same to circulate over a given length of time.

The system is returned to its normal operational mode, simply by disconnecting the suction hoses from the cycling unit 42. The return pipe 46' then becomes inactive, while still containing a minor quantity of stationary cleansing fluid.

In normal operation of the apparatus, the water cleansed therein is discharged downstream of the non-return valve 47 to the outlet 57 through the line 55,56. A valve can be connected at the location 58, for guiding the liquid to the outlet line 55,56. In the illustrated embodiment the location 58 has the form of a T-pipe, and during circulation of the cleansing fluid the fluid will pass downwardly under the inherent pressure of the water column and the vacuum created by the suction hoses. As beforementioned, the cleansing fluid should be mixed with air. Since cleansing fluid has a greater or lesser foaming tendency, especially in view of the intensive processes effected in the apparatus 40, it is essential to ensure that air evacuated through the pipe 51 does not become mixed with liquid (foam) capable of entering the suction motor. To this end there is provided an overfill guard (not shown) in or near the evacuation opening (FIG. 1). This overfill guard should be of a kind which reacts to any form of liquid and particularly to liquid in foam form.

The apparatus according to the invention can also be used for other purposes other than dental surgery purposes, for example in hospital surgical theatres or surgeries.

What I claim is:

1. Apparatus for extracting air and solids from a liquid suspension thereof, comprising
   a vessel assembly which includes a first upper chamber incorporating a dry vessel section and connected to and co-axial with second and third underlying chambers and
   a tangential suspension inlet port merging into said first chamber;
   an air exhaust port communicating with said first chamber at a higher level than said inlet port and connectable to a negative pressure source for establishing a partial vacuum in said vessel;
   liquid outlet means located in the second chamber for removal of cleansed liquid from the vessel;
   centrifuge means located at the juncture between said second chamber and said third chamber and co-axial therewith;
   the portions of said first and second chambers extending between said suspension inlet port and said centrifuge means cooperating to define a cylindrical cyclone wall;
   drive means effective to rotate said centrifuge means;
   solids collecting means located beneath said centrifuge means in said third chamber and effective to receive extracted solids when the centrifuge is brough to a standstill;
   combined guide and anti-splash guard means located in said first chamber adjacent said suspension inlet port and effective to guide said suspension into said second chamber and prevent said suspension entering said dry section; and further guide means arranged in said second chamber and operative in guiding said suspension into the centrifuge means and in guiding cleansed liquid from said second chamber to said liquid outlet means.

2. Apparatus according to claim 1, wherein the first guide means comprises an annular skirt connected to a sleevelike element depending from an upper end wall of the first chamber, and wherein said air exhaust port is located within an annular space defined radially by said skirt and said sleeve-like element.

3. Apparatus according to claim 2 wherein said skirt has a bifurcate configuration and extends downwardly and outwardly past the suspension inlet port.

4. Apparatus according to claim 1, wherein said drive means is a motor having a drive shaft which extends centrally through said first and second chambers and which is arranged to co-act with a perforated air-through-flow disc located at the juncture between said first and second chambers, and with propeller means spaced axially from said disc and located within said second chamber radially inwards of said second guide means, to leave a narrow annular gap therebetween.

5. Apparatus according to claim 1, wherein said further guide means comprises an annular angled member which is connected to the wall of said second chamber, which carries on an upper arm section thereof mutually spaced arcuate guide vanes which terminate short of said drive shaft, and a lower depending arm section of which forms a sleeve-like skirt within which radially extending propeller means are located, said propeller means being driven by said drive shaft and terminating short of said lower arm section to leave a narrow angular gap therebetween.

6. Apparatus according to claim 5, wherein the centrifuge means has an inverse conical configuration; wherein the depending sleeve-like skirt projects into said inverted conical chamber; and wherein a liquid discharge port is provided radially outwardly of said sleeve-like skirt section of said angled annular member, said port communicating with said liquid outlet means.

7. Apparatus according to claim 1, wherein means are provided in the region of the collecting vessel for preventing rotation of the contents thereof.

8. An apparatus according to claim 1 wherein the drive means is an A.C.-motor, and wherein means are provided for applying, when current to the motor is disconnected, a d.c. pulse effective to reduce the speed of the rotating members in the vessel to zero in fractions of a second.

9. Apparatus according to claim 1, wherein said third chamber is detachably connected to said second chamber.

10. Apparatus according to claim 1, wherein said second chamber is detachably connected to said first chamber.

11. Apparatus for extracting air and solids from a liquid suspension thereof received from the treatment room of a dental surgery, comprising
    a vessel assembly which includes a first upper chamber incorporating a dry vessel section and connected to and co-axial with second and third underlying chambers and a tangential suspension inlet port merging into said first chamber;
    an air exhaust port communicating with said first chamber at a higher level than said inlet port and connectable to a negative pressure source for establishing a partial vacuum in said vessel;
    liquid outlet means located in the second chamber for removal of cleansed liquid from the vessel;
    centrifuge means located at the juncture between said second chamber and said third chamber and co-axial therewith;
    the portions of said first and second chambers extending between said suspension inlet port and said centrifuge means cooperating to define a cylindrical cyclone wall;
    drive means effective to rotate said centrifuge means;

solids collecting means located beneath said centrifuge means in said third chamber and effective to receive extracted solids when the centrifuge is brought to a standstill;

combined guide and anti-splash guard means located in said first chamber adjacent said suspension inlet port and effective to guide said suspension into said second chamber and prevent said suspension entering said dry section;

further guide means arranged in said second chamber and operative in guiding said suspension into the centrifuge means and in guiding cleansed liquid from said second chamber to said liquid outlet means; and a suction unit and/or a water-flushed cuspidor connected with a vacuum line through a recycling connection, said line being connected in turn to the suspension inlet port of said vessel assembly and in which the liquid outlet means is connected to a return line, the closed system thus formed receiving cleansing and/or disinfecting fluid from one of the sources of contaminated liquid connected to the suspension inlet port.

12. An apparatus according to claim 11, wherein means are provided for introducing air into the closed system.

* * * * *